United States Patent
White et al.

(10) Patent No.: US 7,140,367 B2
(45) Date of Patent: Nov. 28, 2006

(54) CONDUIT OVERHEATING DETECTION SYSTEM

(75) Inventors: Craig Karl White, Auckland (NZ); Duncan James Rumbold, Auckland (NZ)

(73) Assignee: Fisher & Paykel Healtcare Limited, Auckland (NZ)

( * ) Notice: Subject to any disclaimer, the term of this patent is extended or adjusted under 35 U.S.C. 154(b) by 88 days.

(21) Appl. No.: 10/368,939

(22) Filed: Feb. 18, 2003

(65) Prior Publication Data

US 2003/0154977 A1     Aug. 21, 2003

(30) Foreign Application Priority Data

Feb. 20, 2002    (NZ) .................................... 517342

(51) Int. Cl.
*A61M 16/00*    (2006.01)

(52) U.S. Cl. ........................... 128/204.17; 128/203.26

(58) Field of Classification Search ........... 128/204.17, 128/204.15, 203.26, 200.14, 203.12, 203.13, 128/203.14, 203.17, 203.27, 911, 201.13; 431/240
See application file for complete search history.

(56) References Cited

U.S. PATENT DOCUMENTS

| | | | |
|---|---|---|---|
| 4,621,632 A | * | 11/1986 | Bartels et al. ......... 128/203.27 |
| 4,708,831 A | | 11/1987 | Elsworth et al. |
| 5,392,770 A | | 2/1995 | Clawson et al. |
| 5,537,996 A | | 7/1996 | McPhee |
| 6,107,611 A | * | 8/2000 | Jones ......................... 219/509 |
| 6,272,933 B1 | | 8/2001 | Gradon et al. |

FOREIGN PATENT DOCUMENTS

EP        1014527        6/2000

* cited by examiner

*Primary Examiner*—Teena Mitchell
(74) *Attorney, Agent, or Firm*—Trexler, Bushnell, Giangiorgi, Blackstone & Marr, Ltd.

(57) ABSTRACT

This invention relates to respiratory humidifiers and heated breathing conduits used to couple a patient to the humidifier. A conduit overheating detection system for a conduit having heating wire or element is disclosed. The overheating detection system may be utilized with a in a single limb conduit system or dual limb system. In each of these systems the conduit overheating detection system monitors the current in the heating element(s) and alters the power to the heating element(s) to prevent the occurrence the heating element(s) and/or conduit from overheating.

11 Claims, 5 Drawing Sheets

CONDUIT OVERHEATING DETECTION SYSTEM

FIELD OF INVENTION

This invention relates to respiratory humidifiers and heated breathing conduits used to couple a patient to the humidifier. A conduit overheating detection system for the conduit heating wire or element is disclosed.

SUMMARY OF THE PRIOR ART

In order to supply gases to a patient or a person needing such gases, it may sometimes be necessary to first humidify those gases, for example using a respiratory humidifier/ventilator system. In such a case where the gases have been humidified, and therefore laden with water, it is likely that during transport through a conduit to the patient, condensation of that water vapour will occur. In order to overcome this disadvantage it is known to associate a heating wire or element with respiratory humidifier breathing conduits to avoid condensation. Examples of such a heated breathing conduit are disclosed in U.S. Pat. No. 5,537,996 (McPhee) and U.S. Pat. No. 5,392,770 (Clawson et al.).

In parts of conduit that contains a heating wire or element, where a temperature probe is incorporated, it is possible to monitor the conduit temperature directly and detect any over-heating. This over-heating may occur under no-flow circumstances, or if excessive insulation such as a blanket is applied to the conduit. In parts of conduit where (to reduce bulkiness, complexity and cost) no temperature probe is incorporated, safety of the equipment or patient may be compromised. This is due to the increased possibility of the conduit material over-heating and melting if no alternative method of monitoring the conduit temperature is implemented. Furthermore, with no sensor in the conduit, the possibility that the patient will receive high temperature gases is increased.

In respiratory apparatus where a dual limb breathing circuit is used, often only one of the limbs is controlled, while the other simply follows or acts as a "slave" to the controlled limb. Therefore, with no monitoring or control of the "slave" limb, if this limb was disconnected from flow, blocked or covered it could overheat or melt without a user being aware.

SUMMARY OF THE INVENTION

It is an object of the present invention to provide a conduit overheating detection system for a respiratory conduit heating element, which goes some way towards overcoming the abovementioned disadvantages.

Accordingly, in a first aspect, the present invention consists in a conduit overheating detection system for a respiratory conduit including a heating element comprising:

detecting means which includes means to detect the current in said heating element, and control means, including power supply means, which implements an algorithm that causes the control means to:

i) receive input of said current in said heating element from said detecting means, and ii) if said current is outside a safe current region, then reduce the power supplied by said power supply means to said heating element so as to alter the current in said heating element to within said safe current region and prevent occurrence of said conduit and said heating element overheating, then iii) after a predetermined time increase said power supplied by said power supply means to said heating element.

In a second aspect the invention consists in a humidification apparatus for humidifying a gases flow to be supplied to a patient or other person in need of such gases comprising:

humidification chamber means adapted to hold a quantity of water and having an inlet and an outlet to allow said gases flow to pass through said humidification chamber means, heating means provided adjacent said humidification chamber means and adapted to provide heat to said quantity of water in said humidification chamber means in order to provide water vapour to said gases flow passing through said humidification chamber means, said heating means utilising a measurable quantity of power, gases transportation pathway means connected to said outlet of said humidification chamber means to convey said gases flow to said patient or other person in need of such gases, gases transportation pathway heating means that is energisable to supply heat to said gases flow along at least a part of the length of said gases transportation pathway means, detecting means which includes means to detect the current in said gases transportation pathway heating means, and control means, including power supply means, which implements an algorithm that causes the control means to:

i) receive input of said current in said gases transportation pathway heating means from said detecting means, and ii) if said current is outside a safe current region, then reduce the power supplied by said power supply means to said gases transportation pathway heating means so as to alter the current in said gases transportation pathway heating means to within said safe current region and prevent occurrence of said conduit and said heating element overheating, then iii) after a predetermined time increase said power supplied by said power supply means to said gases transportation pathway heating means.

In a third aspect, the present invention consists in a conduit overheating detection system for a respiratory conduit heating element comprising:

a conduit, comprising two limbs, one limb being an inspiratory limb of said respiratory conduit and the other being an expiratory limb of said respiratory conduit, said conduit having a heating element disposed within it, where, in use, the current flowing in the first part of said heating element in said first limb differs to that of the current flowing in the second part of the heating element in said second limb, detecting means which includes means to detect a first current and a second current in said first part of said heating element and said second part of said heating element respectively, and control means which implements an algorithm that causes the control means to:

i) receive input of said first current and said second current from said detecting means, ii) determine the difference between said first current and said second current, and iii) if said current approaches a predetermined limit, then reduce the power supplied by said power supply means to said heating element so as to alter the current in said heating element to retreat from said predetermined limit and prevent occurrence of said conduit and said heating element overheating, then iv) after a predetermined time increase said power supplied by said power supply means to said heating element.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which.

DETAILED DESCRIPTION OF THE PREFERRED EMBODIMENTS

Figure 1:
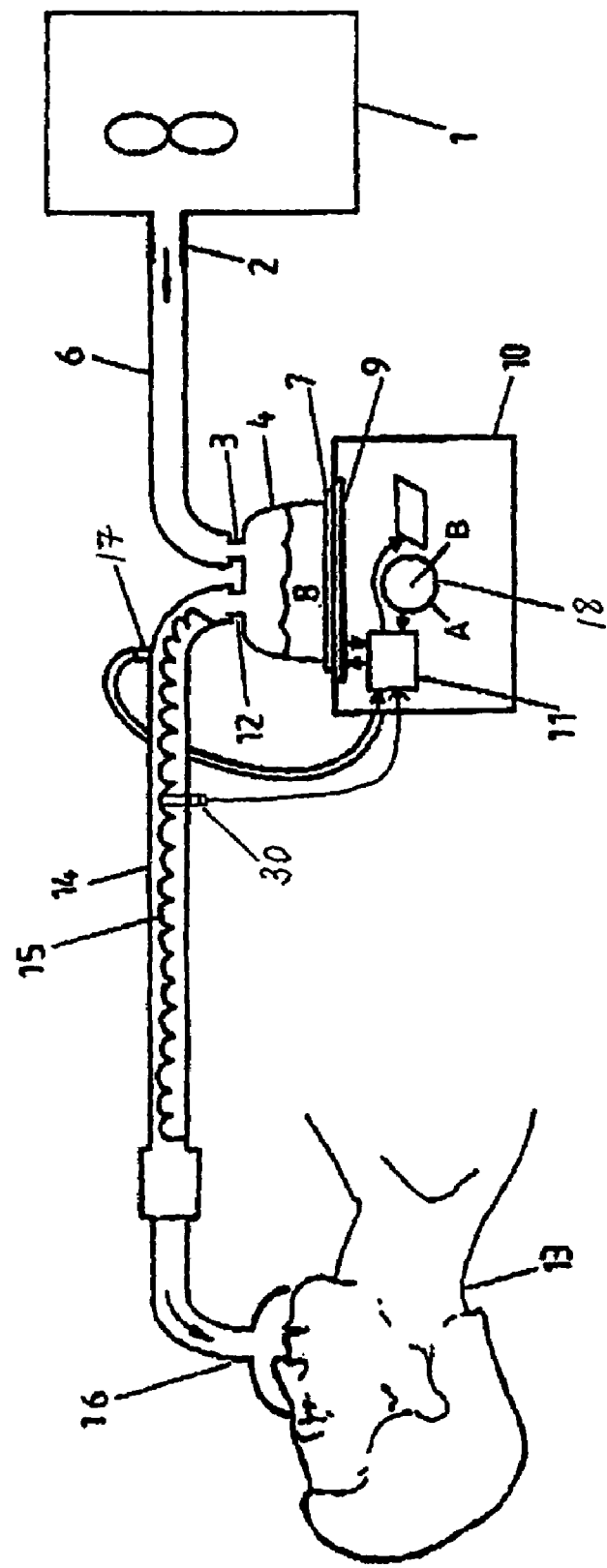
FIG. 1 is a schematic diagram of a respiratory humidification system that may incorporate the detection of conduit overheating system of the present invention.

With reference to the accompanying drawings and in particular to FIG. 1, an example of humidification apparatus or a respiratory humidification system incorporating preferred embodiments of the present invention is illustrated. Included in the respiratory humidification system is a gases supply means 1 (such as a ventilator, insufflator or blower) having an outlet 2, which supplies gases (for example oxygen, anaesthetic gases or air) to the inlet 3 of a humidification chamber means 4 via a conduit 6. Humidification chamber means 4 may, for example comprise a plastics formed chamber having a metal base 7 sealed thereto. Humidification chamber 4 is adapted to hold a volume of water 8, which is heated by a heater plate means 9 under the control of controller or control means 11 of a humidification device or humidifier 10.

As the water within chamber 4 is heated it will slowly evaporate, mixing water vapour with the gases flow through the humidification chamber from ventilator 1. Accordingly, humidified gases leave humidification chamber 4 via outlet 12 and are passed to a patient or other person in need of such gases 13 through a gases transportation pathway or inspiratory conduit 14. In order to reduce condensation within the inspiratory conduit 14 and to raise the temperature of the gases provided to the patient 13 a heating element means 15 is provided which is energised under the control of control means 11.

In FIG. 1 a gases mask 16 is shown over the patient's nose and mouth (referred to as "Intact Airways" gases delivery) however it should be understood that many gases delivery configurations exist such as intubation in which a delivery tube is positioned in the patient's trachea to by-pass the patient's airways (known as "Intubated Airways" gases delivery). It is also possible to provide a return path for the patient's exhaled gases back to ventilator 1. In this case a suitable fitting such as a "Y-piece" 36 (see FIG. 6) may be attached between a patient 40 inspiratory conduit 31 and an expiratory conduit 32, which is connected to an inlet 42 of the ventilator 33.

Control means 11 may for example comprise a microprocessor or logic circuit with associated memory or storage means which holds a software program which, when executed by control means 11, controls the operation of the humidification system in accordance with instructions set in the software and also in response to external inputs. For example, control means 11 may be provided with input from heater plate 9 so that control means 11 is provided with information on the temperature and/or power usage of the heater plate 9. Furthermore, a flow sensing means or flow probe 17 may be provided anywhere in the breathing circuit ("the breathing circuit" comprises the parts of the humidification apparatus through which the gases flow passes). The flow probe 17 is shown in FIG. 1 may be provided at or near the humidifier outlet 12 to indicate to control means 11 the outlet gases flow. Also provided in such apparatus may be a temperature probe at the outlet to the humidifier and an ambient temperature probe at the inlet to the humidifier. Each of the outputs from these probes may be an input to control means 11.

A still further input to control means 11 may be a user input means or switch 18 which could be used to allow a user (such as a health care professional or the patient themselves) to set a desired gases temperature of gases to be delivered or a desired gases humidity level to be delivered or alternatively other functions could be controlled by switch 18 such as control of the heating delivered by heating element 15 or selecting from a number of automatic gases delivery configurations.

Figure 2:
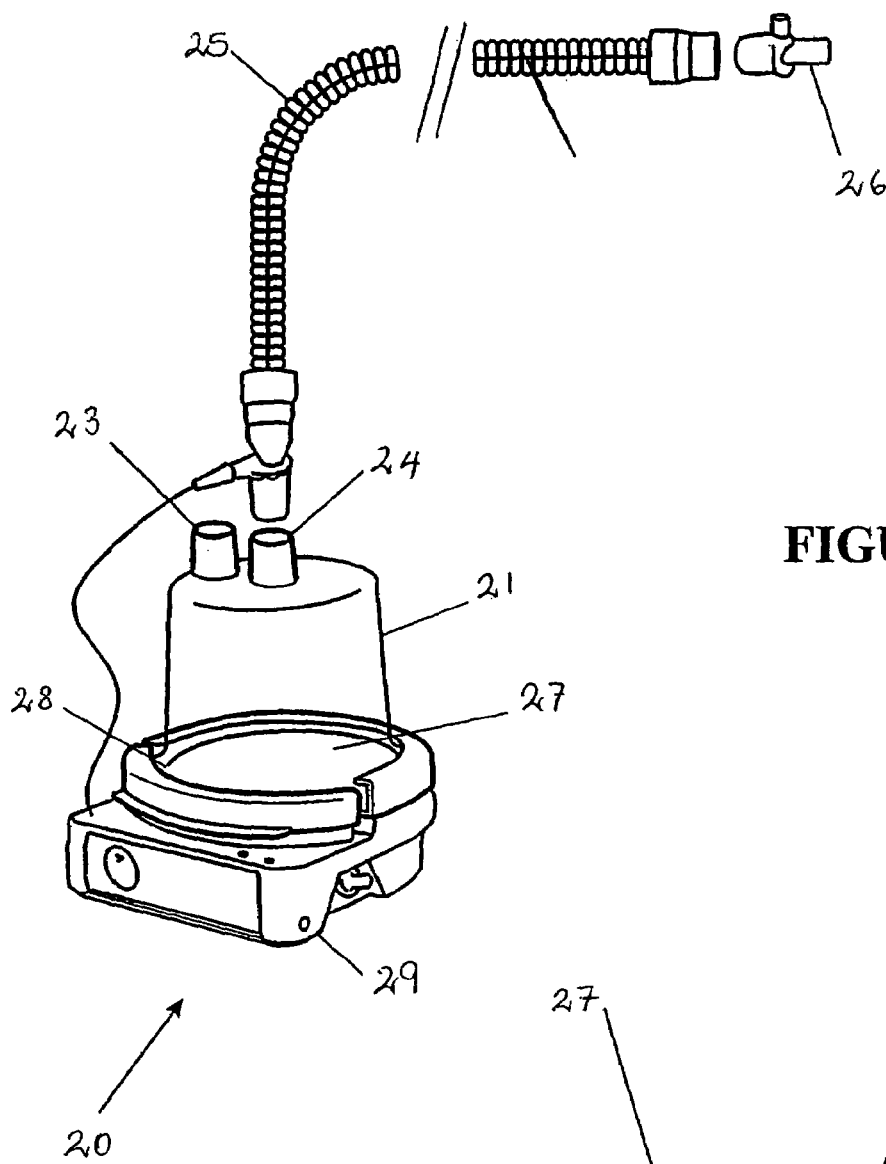
FIG. 2 is an illustration of a respiratory humidifier system that may utilise the overheating detection system of the present invention.
Figure 3:
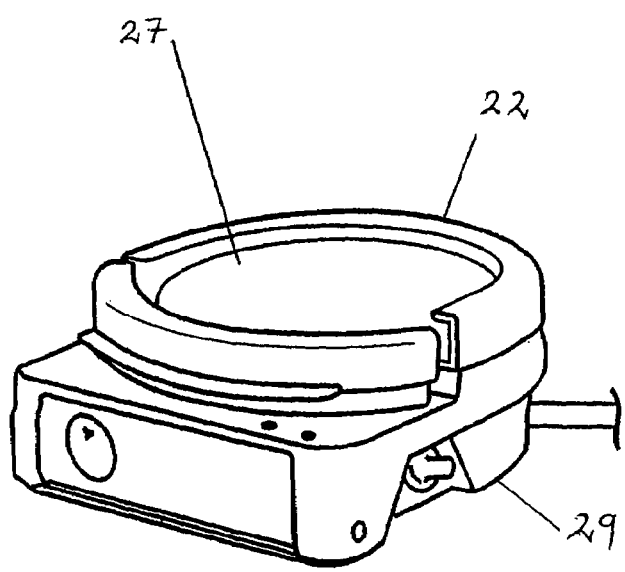
FIG. 3 is an illustration of the humidifier base of the respiratory humidifier system of FIG. 2.

Referring to FIGS. 2 and 3 that show a humidifier apparatus 20 in more detail, the humidifier 20 has a humidifying chamber 21 having edges that engage with the collar 22 on the humidifier 20. The gases to be humidified may be a mixture of air, oxygen and anaesthetic for example, which are supplied to the chamber through gas inlet 23. This might be connected to a ventilator, source of pressurised oxygen, flow generator, or air compressor. A gases outlet 24 is also provided and the gases outlet 24 is connected to the conduit 25, which conveys humidified gases to the patient at the end 26 of the conduit. The end 26 of the conduit may have a cannula connected to the patient's nose, nasal mask or face mask connected to the patient's face, so as to supply humidified gases to the patient. The humidifier heater plate 27 has a temperature transducer 28 that is in electrical connection with the electronic control circuitry in body 29 of the apparatus so that the control means monitors the temperature of the heating plate.

A heating element means 15 is provided within the conduit 25 to help prevent condensation of the humidified gases within the conduit. Such condensation is due to the temperature of the walls of the conduit being close to the ambient temperature, (being the temperature of the surrounding atmosphere) which is usually lower than the temperature of the humidified gases within the conduit. The heating element 15 effectively replaces the energy lost from the gases through conduction and convection during transit through the conduit. Thus the conduit heating element 15 ensures the gases delivered are at an optimal temperature and humidity.

The heating element 15, which is usually a copper filament, has a material property that causes a change in electrical resistance, which is usually significant, when there is a change in temperature of the copper filament. Therefore, the electrical resistance, and indirectly the temperature of the heating element 15 can be monitored by monitoring the current drawn by the heating element 15 when power is applied to the heating element 15. This monitoring of the heating element 15 may be done by directly using the control means 11, which is connected to the heating element 15, or by external detection means, such as a sensor 30 (see FIG. 1) connected to the control means 11. If the current through the heating element 15 is low then the resistance of the heating element 15 is high, and the heating element temperature is high and the conduit hot. In which case, if the current drawn by the heating element 15 exceeds a predetermined limit or is outside a safe current region, the respiratory humidifier 10 and conduit 14 can be switched to a safe mode by the control means 11, and then back into operating mode once the temperature of the heating element 15 has reduced to safe levels.

Figure 4:
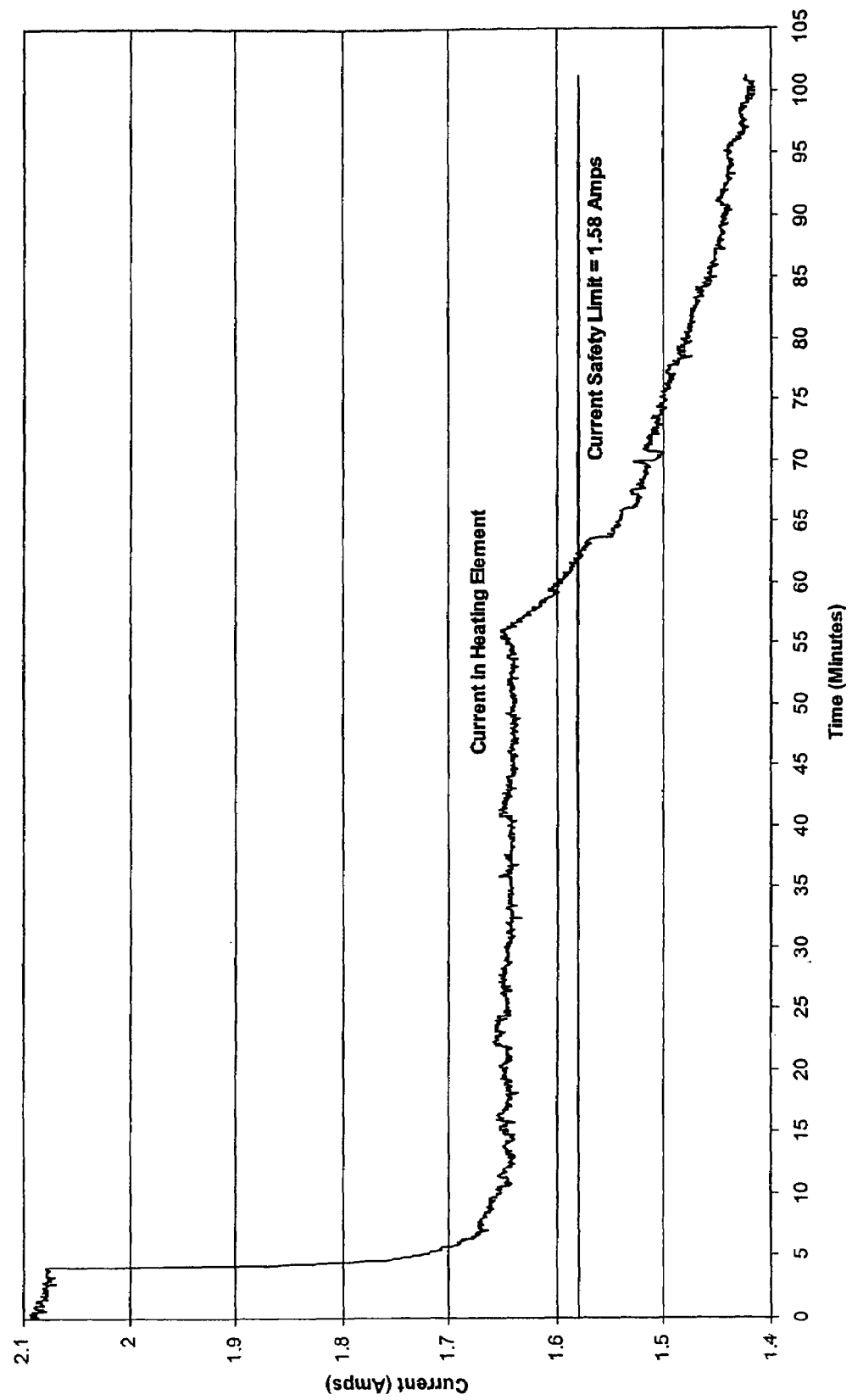
FIG. 4 is a graph of the current in a heating element over time during the testing of a conduit under conditions where there is no current detection.

Whether the predetermined conduit heating element current limit is an upper or a lower limit depends on the specific resistance-temperature characteristic of the heating element material. FIG. 4 shows a graph of current (in amperes) versus time for a conduit with heating element where the element is a typical copper filament. In order to simulate an increase in the temperature of the conduit, tests were conducted where a blanket was placed over the conduit at time t=55 minutes and no detection of conduit overheating was used.

As can be seen from FIG. 4, between 0 to 4 minutes the conduit heating element is in its start-up period and is not significantly powered to cause heating of the humidified gases. Between 4 and 55 minutes the conduit heating element power has been set to a constant duty cycle (in this instance the duty cycle was 95%, but any appropriate level is sufficient) and the heating element current settled at a stable operating level, in this example the operating level is approximately 1.65 amperes, other operating levels appropriate to the heating element may be used. The current operating level ultimately depends upon the flow rate, ambient temperature and conduit dynamics (that is, the dimensions, materials, resistance and wire length of the heating element). However, testing has shown that for a particular conduit design, a current safety limit can be determined, below which the conduit heating element current will not fall (at any flow rate or ambient temperature) unless the conduit is heating to a degree that approaches a safety hazard.

In FIG. 4 at time t=55 minutes, during testing, a blanket was placed over the conduit, this additional insulation caused the current within the heating element to decrease as the temperature within the conduit increased. As can be seen the current in the heating element between t=55 minutes and t=100 minutes continues to decrease below the predetermined current safety limit. Eventually, at time t=100 minutes the conduit temperature is such that the conduit, being made from a plastics material, begins to melt. Also over the period of time where the heating element current is below that of the current safety limit if such a respiratory system was used under these conditions then the patient is likely to be supplied with high temperature gases, causing discomfort and possibly harm to the patient.

The method of detecting over-heating of the heating element 15 in the conduit 14 is to monitor the current in the heating element 15 as described above. To prevent unsafe conduit temperatures and eventual conduit melt a heating element current safety limit can be determined, by manual testing or the like, and programmed into the control means 11. When the current in the heating element 15 exceeds the current safety limit, the humidifier 10 is switched to a safe mode by the control means 11, decreasing the heating element power to a predetermined safe level for a predetermined time period, then increasing the heating element power to normal operating mode or level.

Figure 5:
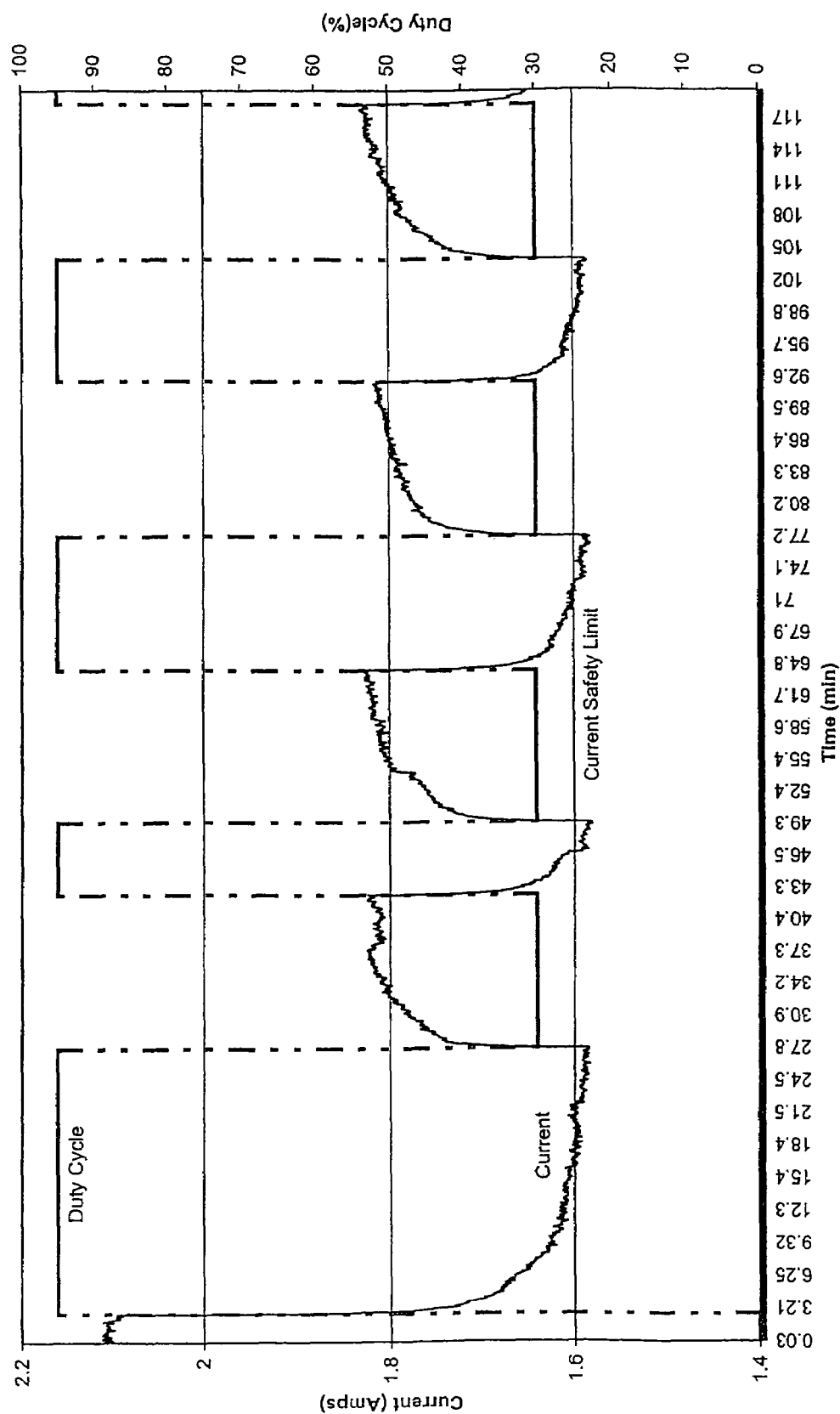
FIG. 5 is a graph of the current in a heating element over time where current detection is used to ensure that the conduit does not melt and gases provided to the patient are not of high temperature.

In the present invention the safe mode is one where the duty cycle power to the heating element 15 has been reduced from the operating value. As can be seen in FIG. 5 when the current in the heating element drops below the current safety limit, this is detected by a detecting means, such as a sensor 30, the reduction of current causes the control means 11 to limit the duty cycle of the voltage supplied to the heating element, in this case the duty cycle has been reduced to approximately 30%, but other appropriate values may be used. The effect of reducing duty cycle is to increase the current in the heating element. The control means 11 which may be either a software program stored in a micro controller or may be electronically implemented by a comparator and current limiting circuit.

FIG. 5 shows the current and duty cycle waveforms where the current drops below the current safety limit four times, and each time the detector and controllers act to alter the duty cycle and thus bring the heating element current to safe levels. Preferably the heating element is run at the 30% duty cycle for approximately 15 minutes (although, other appropriate values may be used) before returning to the normal operating mode. Further, if the current limit is again reached then the present invention will act to ensure that the apparatus moves into safe mode operation, reducing the duty cycle and increasing the current in the heating element.

Figure 6:
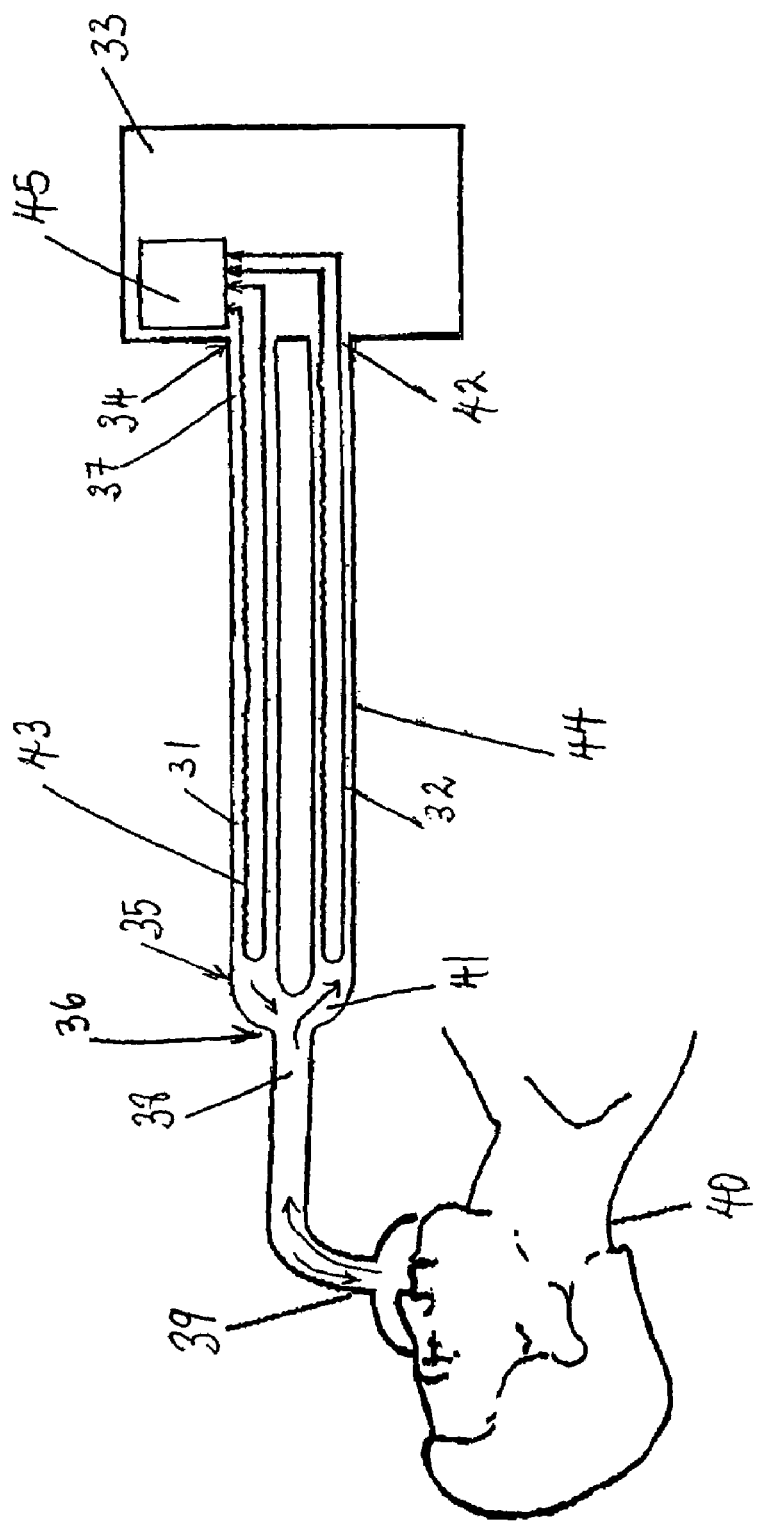
FIG. 6 is a schematic diagram of a respiratory humidification system having inspiratory and expiratory conduits, which may incorporate the detection of conduit overheating system of the present invention.

In a second embodiment where the respiratory apparatus, incorporating the overheating detection system of the present invention comprises two conduits (such as that shown in FIG. 6), where one conduit is an inspiratory conduit and the other the expiratory conduit, the present invention has a different embodiment. Referring now to FIG. 6, an inspiratory conduit 31 is connected to a ventilator and/or humidifier. In FIG. 6, the inspiratory conduit 31 is merely connected at it's proximal end 37 to a ventilator 33, but in most preferred embodiments a humidifier (such as that described in relation to FIGS. 1 to 3 is placed between the ventilator exit port 34 and inlet to the inspiratory conduit 31. The distal end 35 of the inspiratory conduit 31 is connected to a "Y" shaped connector 36 having three inlet/outlet ports. One port 38 of the "Y" shaped connector 36 directs the inspiratory gases flowing through the inspiratory conduit 31 to a patient interface 39 and patient 40 and also received air or gases exhaled from the patient 40. The expired air is channelled by the "Y" shaped connector 36 to an expiratory conduit 32 via the third port 41 of the "Y" shaped connector 36 so that the expiratory gases may be returned to the ventilator 33 from the end 42 of the expiratory conduit 31. In the preferred form each of the inspiratory 31 and expiratory 32 conduits has a heating element (31, 32 respectively) residing within, throughout or about it. These heating elements are of the type as described above in relation to FIG. 1. In common ventilator systems the duty cycle of the voltage to the heating elements 43, 44 within the conduits 31, 32 is usually controlled using inputs, such as conduit temperature from the inspiratory conduit, while the expiratory conduit acts as a slave. Therefore, in order to detect and control any overheating of the expiratory conduit 32, the current in each of the inspiratory 31 and expiratory 32 conduits need to be detected. Usually, the electrical resistance in each of the heating elements 43, 44 within the conduits is different to allow different heating levels during operation; because of this a different current flows through each conduit. Thus, the detecting means, such as a sensor (not shown) or a control means 45, must be capable of detecting the current in both conduits 31, 32. In this embodiment it is preferred that the current in the heating elements 43, 44 is detected by the control means 45, which compares each of the currents. If the difference between the detected currents in the heating elements 43, 44 starts to approach a predetermined limit the control means 45 causes the heating elements 31, 32 to be switched to the safe operation mode in the same manner as described above (in relation to the first embodiment of FIG. 1). In this way, if either of the conduits 31, 32 is covered during use, or if gases are not flowing in one conduit causing that conduit to overheat, then overheating will be detected and the duty cycle of the voltage supplied to the heating elements 43, 44 will be altered by the control means 45 to cause the currents in the heating elements 43, 44 to return to safe levels, preventing damage to the conduits 31, 32 or harm to the patient 40.

The predetermined limit of the difference in current between the conduits 31 32 depends on the specific resistance-temperature characteristic of the heating element material, and the relative resistances of the inspiratory 31 and expiratory 32 conduits. For example, if the inspiratory conduit heating element 43 has a resistance of 18 ohms and the expiratory conduit heating element 44 has a resistance of 12 ohms, where the heating element is a typical copper filament, the difference in operating currents between the conduits 31, 32 is approximately 0.4 amperes. If the expiratory conduit 32 overheats, the current in the expiratory conduit heating element 44 will reduce while the current in the inspiratory conduit heating element 43 remains unaffected. Therefore, the difference in current between the heating elements 43, 44 will reduce. In the example given above, the predetermined limit referred to is a difference in current between the conduits of 0.3 amperes.

We claim:

1. A conduit overheating detection system for at least one respiratory conduit comprising:
    at least one respiratory conduit including at least one heating element, said respiratory conduit in use providing gases to or from a patient,
    a detector to detect the current in said at least one heating element, and
    a controller, incorporating said detector such that said heating element is connected to said controller, and including at least one power supply, which implements an algorithm that causes said controller to:
    i) receive input of said current in said at least one heating element from said detector, and
    ii) if said current is outside a safe current region, then reduce the power supplied by said at least one power supply to said at least one heating element so as to alter the current in said heating element to within said safe current region and prevent occurrence of said conduit and said at least one heating element overheating, then
    iii) after a predetermined time increase said power supplied by said at least one power supply to said heating element.

2. A conduit overheating detection system according to claim 1 wherein said conduit is a single conduit provided between a medical or respiratory apparatus and said patient.

3. A conduit overheating detection system according to claim 2 wherein said medical or respiratory apparatus is a ventilator and a humidifier is connected between said ventilator and said inspiratory conduit to heat and humidify gases flowing from said ventilator and through said inspiratory conduit.

4. A conduit overheating detection system according to claim 1 wherein said conduit is at least one inspiratory conduit and at least one expiratory conduit provided between a medical or respiratory apparatus and said patient.

5. A conduit overheating detection system according to claim 4 wherein said medical or respiratory apparatus is a ventilator and a humidifier is connected between said ventilator and said inspiratory conduit to heat and humidify gases flowing from said ventilator and through said inspiratory conduit.

6. A conduit overheating detection system according to claim 1 wherein said algorithm is a software program.

7. A conduit overheating detection system according to claim 1 wherein said algorithm is electronically based.

8. A conduit overheating detection system according to claim 1 wherein said safe current region is dependent on at least a previously detected value of said at least one current.

9. A conduit overheating detection system according to claim 1 wherein said safe current region is a set current limit based on prior testing or a look-up table.

10. A conduit overheating detection system according to claim 1 wherein said at least one conduit comprises first and second conduit limbs, the first limb being an inspiratory limb and the second limb being an expiratory limb, said at least one heating element is a first heating element in said inspiratory limb and a second heating element in said expiratory limb.

11. A conduit overheating detection system according to claim 10 wherein said algorithm additionally causes said controller to:
    receive input of said current in each of said first and second heating elements from said detector, and
    determine the difference between said first current and said second current, then if said difference is outside said safe current region then reduce the power supplied by said at least one power supply to said first and second heating elements so as to alter the current in said first and second heating elements to within said safe current region.

* * * * *